United States Patent [19]

Tanaka et al.

[11] Patent Number: 4,871,679
[45] Date of Patent: Oct. 3, 1989

[54] INTEGRAL MULTILAYER ANALYTICAL ELEMENT FOR DETERMINING CALCIUM AND ITS USE

[75] Inventors: Mitsutoshi Tanaka; Fuminori Arai; Kaoru Terashima; Nakatsugu Yaginuma, all of Saitama, Japan

[73] Assignee: Fuji Photo Film Co., Ltd., Kanagawa, Japan

[21] Appl. No.: 73,759

[22] Filed: Jul. 15, 1987

[30] Foreign Application Priority Data

Jul. 15, 1986 [JP] Japan ................. 61-164570
Jul. 18, 1986 [JP] Japan ................. 61-168091

[51] Int. Cl.$^4$ .................. G01N 33/20; G01N 31/22
[52] U.S. Cl. ................... 436/79; 436/170; 422/56; 422/57
[58] Field of Search ................... 422/56–58; 436/79, 170

[56] References Cited

U.S. PATENT DOCUMENTS

| | | | |
|---|---|---|---|
| 3,938,954 | 2/1976 | Stavropoulos et al. | 436/79 |
| 3,992,158 | 11/1976 | Przybylowicz et al. | 422/57 |
| 4,166,093 | 8/1979 | Smith-Lewis | 422/56 |
| 4,361,648 | 11/1982 | Shuenn-tzong | 435/10 |
| 4,540,670 | 9/1985 | Arai et al. | 435/805 |
| 4,557,901 | 12/1985 | Koyama et al. | 422/56 |
| 4,594,225 | 6/1986 | Arai et al. | 422/56 |

FOREIGN PATENT DOCUMENTS

| | | |
|---|---|---|
| 0158993 | 10/1985 | European Pat. Off. |
| 3332315 | 3/1984 | Fed. Rep. of Germany |
| 1191966 | 8/1986 | Japan .................. 436/170 |

Primary Examiner—Michael S. Marcus
Assistant Examiner—Rebekah A. Griffith
Attorney, Agent, or Firm—Jules E. Goldberg

[57] ABSTRACT

A method of preparing an integral multilayer analytical element such as for analysis of calcium comprising a water-impermeable light-transmissive support, a reagent layer containing a water-soluble indicator capable of reacting with an analyte to produce an optically detectable change, and a porous spreading layer containing a spreading action controller and/or an acid capable of decomposing the calcium compounds in a sample, superposed in this order, wherein the spreading action controller and/or the acid is dissolved in an organic solvent which does not dissolve the above water-soluble indicator, this solution is incorporated into the porous spreading layer, and this superposed material is dried. In the method of the present invention, the migration of the water-soluble indicator in the reagent layer at the time of incorporating the spreading action controller or the acid into the spreading layer is inhibited by using a particular organic solvent. Migrations of the indicator and colored material to the spreading layer are also lowered by the spreading action controller, and by these, analytical accuracy of the analytical element is improved. In the case of the analytical element for analysis of calcium, permeation of the acid into other layers than the spreading layer is inhibited, and permeation of a pH buffer in other layer(s) into the spreading layer is also inhibited by using a particular organic solvent. As a result, effective decomposition of calcium compounds in a sample and effective coloration can be achieved.

3 Claims, No Drawings

INTEGRAL MULTILAYER ANALYTICAL ELEMENT FOR DETERMINING CALCIUM AND ITS USE

BACKGROUND OF THE INVENTION

1. Field of the Invention

This invention relates to a method of preparing an integral multilayer analytical element for analysis of an analyte in a liquid sample. More particularly, this invention relates to an improvement of a method of preparing a dry-type integral multilayer analytical element for analysis of an analyte in a liquid sample, such as, a biological body fluid, including blood (whole blood, blood plasma, blood serum), cerebrospinal fluid, lymph, saliva and urine, and which is useful for diagnosis in the clinical field.

2. Description of the Prior Art

Various integral multilayer analytical elements have been known. However, in every analytical element, when a water-soluble substance is used as the indicator for reacting with the analyte in a sample to generate an optical change, the indicator diffuses into the upper porous spreading layer and results in a lowering of the analytical accuracy. (This diffusion is called "migration".) In the case that the indicator is highly soluble in water, such as in the case of the analytical element for analysis of calcium, the analytical accuracy is remarkably lowered by the migration. Since the change in the calcium concentration in blood does not vary widely, this defect is fatal for this analytical element.

Therefore, various investigations have been made in order to eliminate the defect. For example, a migration-inhibiting layer can be introduced into the analytical element as disclosed in U.S. Pat. No. 4,166,093. This migration-inhibiting layer inhibits the migration of a water-soluble indicator by immobilizing it with a polymer mordant. However, the mordant often inhibits coloration of the indicator and, accordingly, it is not a fundamental solution to this problem. Besides, the preparation of this layer is difficult, thereby raising the cost of the analytical element.

It is also a problem that an aqueous liquid sample spotted on a porous spreading layer spreads too broadly in this spreading layer. In EP 0,162,302A, hydrophilic cellulose derivatives and nonionic surfactants having an HLB value of more than 10 are disclosed as being effective as a spreading action controller. The hydrophilic cellulose derivative is dissolved in water and applied on the spreading layer. Since the solubility of the nonionic surfactant in water is low, it is dissolved in a mixture solvent of water and acetone.

On the other hand, colorimetry using an indicator is widely employed in the field of clinical analysis. The indicator is usually o-Cresolphthalein Complexone of which the optimum pH for coloration is in the alkaline range, particularly higher than pH 10 where the binding to calcium is stable. Also, it is known that the samples for clinical diagnosis, such as, blood, contain the calcium in a bound state, such as, protein-bound calcium and acid-bound calcium, in addition to the calcium in an ion state. All calcium in the sample is first ionized by an acid treatment, and thereafter, a color reaction is carried out (Clin. Chem. Vol. 29, p. 1497 ( 1983)). This method is, for example, described on pages 148 to 150 of "Jissen Rinsho Kagaku-Zoho Ban (Practical Clinical Chemistry-Revised and Enlarged Edition)" (Kitamura et al., Ishiyaku Shuppan Kabushiki Kaisha, Japan 1982).

An outline of this method is as follows. o-Cresolphthalein Complexone is dissolved in a small amount IN KOH, and glacial acetic acid is added to this solution to prepare an acidic solution 1. An alkaline solution 2 containing potassium acetate-HCl-diethylamine is separately prepared. The solution 1 is added to a sample, and allowed to react. Subsequently, the solution 2 is added to the reaction mixture, and color reaction proceeds. Recently, a one-step type reagent kit has also been available ("Agent Calcium", OINABBAT, U.S.A.). It has been reported that a linear relation between absorbance and concentration is obtained by allowing citric acid, its salt, or mixtures thereof, to coexist throughout the reaction (Japanese Patent Kokai No. 57-154058). However, in this patent, citric acid is used in a concentration of 0.01 to 0.05 M/l in an alkaline condition, such as, pH 10 to 11, but this acid is not utilized for acidification of the sample nor the color reaction.

In the case of the analytical element for analysis of calcium, in order to decompose the bound state of calcium, the pH of the upper layer is made lower than 5, usually pH 1 to 2. On the other hand, the optimum reaction pH of preferable indicators, such as, o-Cresolphthalein is usually higher than pH 10. Since it is difficult for such a high pH layer to coexist with the low pH layer in a thin analytical element, the coloring reaction was set to proceed at about pH 5.5. Chlorophosphonazo-III and Arsenazo-III were used as the indicator. However, in this analytical element, the absorbance of the background is high, such as, higher than 2 and the measurement is carried out at a long wave length (near 680 nm). Accordingly, the analytical accuracy becomes worse.

SUMMARY OF THE INVENTION

An object of the invention is to provide a method of preparing an integral multilayer analytical element using a water-soluble indicator where migration of the indicator does not occur and thereby the accuracy of measurement is maintained.

Another object of the invention is to provide a method of preparing an integral multilayer analytical element using a water-soluble indicator easily without lowering the accuracy of the measurement.

Another object of the invention is to provide a method of preparing an integral multilayer analytical element using a water-soluble indicator inexpensively without lowering the accuracy of the measurement.

Another object of the invention is to provide a method of preparing an integral multilayer analytical element capable of determinating total calcium concentration easily without pretreatment by treating with acid in the analytical element and subsequently allowing to react to form color.

Another objection of the invention is to provide a method of preparing an integral multilayer analytical element using a water-soluble indicator capable of determinating total calcium concentration with high accuracy.

Another object of the invention is to provide a method of easily preparing an integral multilayer analytical element capable of determinating total calcium concentration having the above characteristics.

Another object of the invention is to provide an integral multilayer analytical element capable of determinating total calcium concentration having the above characteristics.

Still another object of the invention is to provide a method of measuring total calcium concentration of an aqueous sample easily and rapidly by using such an integral multilayer analytical element.

The present inventors have investigated in order to achieve such objects and found that the migration of a water-soluble indicator can be inhibited by dissolving a spreading action controller and/or an acid in an organic solvent which does not dissolve the water-soluble indicator, and incorporating the spreading action controller and/or the acid into the porous spreading layer, such as, by the application of the above spreading action controller and/or the acid solution on the spreading layer.

Thus, the present invention provides a method of preparing an integral multilayer analytical element comprising a water-impermeable light-transmissive support, a reagent layer containing a water-soluble indicator capable of reacting with an analyte to produce an optically detectable change, and a porous spreading layer containing a spreading action controller and/or an acid, superposed in this order, comprising dissolving the spreading action controller and/or the acid in an organic solvent which does not dissolve the above water-soluble indicator, incorporating this solution into the porous spreading layer, and drying this superposed material.

DESCRIPTION OF THE PREFERRED EMBODIMENTS

As the water-impermeable light-transmissive support, a known support employed in an usual multilayer analytical element may be employed. Such a support is a film, a sheet or a flat plate having a thickness of about 50 $\mu$m to about 1 mm, preferably, about 80 $\mu$m to about 0.3 mm and capable of transmitting the object light being the wave length range of about 200 nm to about 900 nm. Such a support may be made from a polyester (for example, polyethylene terephthalate or polycarbonate of bisphenol A), a cellulose ester (for example, cellulose diacetate, cellulose triacetate or cellulose acetate propionate), or polystyrene. The optical property of the support may be controlled by suspending light-reflective or light-absorptive particles, such as, titanium dioxide particles, barium sulfate particles or carbon black therein. A known undercoating layer or a known adhesive layer may be provided on the surface of the support in order to secure the adhesion of the support to the reagent layer, a water-absorption layer or the like, superposed on the support.

The reagent layer is water-absorptive and water-permeable and comprises a hydrophilic polymer as a polymer binder and a reagent composition containing at least an indicator capable of reacting with the analyte in an aqueous sample to produce an optically detectable change uniformly dispersed therein.

The hydrophilic polymer used in the reagent layer has a swelling ratio in the range from about 150% to about 2,000%, preferably, about 250% to about 1,500% at a water absorption at 30° C. Examples of the hydrophilic polymer are gelatins including acid treated gelatin and deionized gelatin, gelatin derivatives, such as, phthalated gelatin and hydroxyalkyl acrylate grafted gelatin, agarose, pullulan, pullulan derivatives, polyacrylamide, polyvinyl alcohol and polyvinyl pyrrolidone. They are disclosed in EP 0,119,861A and EP 0,142,849A. Preferable hydrophilic polymers are usually gelatins, gelatin derivatives, polyacrylamide and polyvinyl alcohol, deionized gelatin being is the most preferable.

The thickness of the reagent layer in the dry state is about 5 $\mu$m to about 50 $\mu$m, preferably about 7 $\mu$m to about 30 $\mu$m. The coating weight of the reagent layer itself is about 5 g/m$^2$ to about 50 g/m$^2$, preferably about 7 g/m$^2$ to about 30 g/m$^2$.

The indicator reacts with an analyte to produce an optically detectable change. The wave length used for detection is not limited to the visible region, and includes the ultraviolet region and infrared region. This indicator is water-soluble, and the method of the invention is particularly effective when solubility of the indicator is higher than 5 mg/100 g water at 25° C. On the other hand, it is also necessary that it not dissolve in the organic solvent used for the spreading action controller. Such an indicator is selected from known ones and it may form a complex with an analyte.

The analyte includes calcium, magnesium, inorganic phosphorus and iron. These exist in an ionic state, a salt of a fatty acid, a protein conjugate or the like. The above inorganic phosphorus exists in the state of a phosphate acid ion or a phosphate salt. The liquid sample containing such a sample includes various biological fluids, foods, drinks, liquors and medicines.

The indicators for the analysis, of calcium are, for example, described in "Dotite Reagents Catalog" (Dojindo Laboratories, Kumamoto, Japan, 1980). Examples of the indicator are o-Cresolphthalein Complexone (3,3'-bis[[di(carboxymethyl)amino]methyl]-o-cresolphthalein [2411-89-4], optimum pH; about 10.5), Eriochrome Black T(monosodium salt of 1-(1-hydroxy-2-naphthylazo)-6-nitro-2-hydroxynaphthalene-4-sulfonic acid [1787-61-7]), Methylthymol Blue Complexone (tetrasodium salt of 3,3'-bis[[di(carboxymethyl)amino]methyl]thymolphthalein [1945-77-3]), Thymolphthalein Complexone (3,3'-bis[[di(carboxymethyl)amino]methyl]thymolphthalein [1913-93-5]), Arsenazo-III(2,7-bis[(2arsonophenyl)azo]-1,8-dihydroxynaphthalene-3,6-disulfonic acid [1668-00-4]) and Chlorophosphonazo-III)2,7-bis[(4-chloro-2-phosphonophenyl)azo]-1,8-dihydroxynaphthalene-3,6-disulfonic acid [1914-99-4]). The figures in the brackets represent chemical Abstracts Registry Numbers. Among these, o-Cresolphthalein Complexone and Arsenazo-III are preferred for the most accurate determination of calcium.

In the multilayer analytical element for analysis of calcium, a masking agent for masking magnesium ion is preferably incorporated. Such a masking agent includes 8-hydroxyquinoline, 8-hydroxyquinoline-5-sulfonic acid, 8-hydroxyquinoline sulfate and the like. Suitable layers for incorporating the masking agent are the reagent layer and/or its upper (far from the support) adhesive layer or the spreading layer. The content of the masking agent is about 1.5 to about 10 times, preferably about 2 to about 5 times, the content of the indicator.

The indicator for analysis of magnesium includes Xylidyl Blue I$^R$(monosodium salt of 3-[[3-(2,4-dimethylphenylcarbamoyl)-2-hydroxy-1-naphthyl]azo]-4-hydroxybenzenesulfonic acid [14936-97-1]), and the indicator for analysis of iron includes Bathophenanthroline disulfonic acid.2Na salt(disodium salt of 4,7-bis(4-sulfophenyl)-1,10-phenanthroline). The indicator for analysis of inorganic phosphorus includes p-(methylamino)phenol sulfate.

The reagent composition may be incorporated into two or more layers, for example, the reagent layer and a water-absorption layer.

In the reagent layer, a pH buffer may also be incorporated in order to maintain the reaction with the indicator at its optimum. This pH is different according to each reaction, and in the case of analyzing calcium using o-Cresolphthalein as the indicator, the optimum pH is at 9 to 10.5. The pH buffers suitable for integral multilayer analytical elements are described in "Kagaku Benran Kiso-Hen" pp 1312–1320, Maruzen, Tokyo, 1966, R. M. C. Dawson et al, "Data for Biochemical Research", 2nd Ed., pp 476–508, Oxford at the Clarendon Press, 1969, "Biochemistry", Vol. 5, from p. 467, 1966 and "Analytical Biochemistry", Vol. 104, pp 300–310, 1980. The pH buffer in the range of pH 8.0 to 11.0, particularly, pH 9.0 to 10.5, includes buffers containing tris(hydroxymethyl)aminomethane, buffers containing a phosphate, buffers containing a borate, buffers containing a carbonate, buffers containing glycine and the like. Examples are N,N-bis(2-hydroxyethyl)glycine (Bicine), sodium or potassium salt of N-2-hydroxyethylpiperazine-N'-2-hydroxypropane-3-sulfonic acid (HEPPS), sodium or potassium salt of N-2-hydroxyethylpiperazine-N'-3-sulfonic acid (EPPS), sodium or potassium salt of 3-(cyclohexylamino)-1-propanesulfonic acid (CAPS), sodium or potassium salt of N-[tris(hydroxymethyl)methyl]-3-aminopropanesulfonic acid (TAPS), sodium or potassium salt of N-2-hydroxyethylpiperazine-N'-2-ethanesulfonic acid (HEPES) and a combination of any of them and an acid, an alkali or a salt. Preferable buffers include Tris-sodium borate, Bicine, HEPPS, sodium salt of HEPPS, EPPS, sodium salt of EPPS, CAPS, sodium salt of CAPS, TAPS and sodium salt of TAPS. When gelatin or its derivative is used as the hydrophilic polymer, the pH buffer containing boric acid or sodium borate is preferable in that this layer can suitably be hardened by cross-linking using a cross-linking agent having vinyl sulfone structure. This gelatin or its derivative layer are stable when applied and quantitative analysis can be performed with high accuracy. A known base polymer is also usable as a pH buffer. A surfactant, such as, the nonionic surfactant described later, may also be added to the reagent layer.

The reagent layer is preferably transparent, but its optical property may be controlled by suspending a small amount of titanium dioxide particles, barium sulfate particles or carbon black therein.

The porous spreading layer includes spreading layers of woven fabric disclosed in U.S. Pat. No. 4,292,272 and GB 2,087,074A, such as, plain weaves including broad cloth and poplin, spreading layers of knitted fabric disclosed in EP 0,162,302A, such as, tricot fabric, double tricot fabric and milanese fabric, spreading layers composed of a paper containing fibrous pulp of an organic polymer disclosed in Japanese Patent Kokai No. 57-148250, membrane filters (blushed polymer layer) as disclosed in U.S. Pat. No. 3,992,158, continuous microspaces-containing porous layers where polymer particulates, glass particulates or diatomaceous earth are dispersed in a hydrophilic polymer binder, and continuous microspaces-containing porous layers where polymer particulates, glass particulates, etc. are joined so as to contact with each other at a point by using a polymer adhesive which does not swell in water (three-dimensional lattice structure layer) disclosed in U.S. Pat. No. 4,258,001.

In order to raise the adhesive force, the above fibrous porous spreading layer, such as, woven fabrics, knitted fabrics and papers may be made hydrophilic by a physical activation treatment, such as, glow discharge or corona discharge disclosed in GB 2,087,074A, a chemical treatment, such as, washing, degreasing and immersing in a hydrophilic polymer solution, disclosed in U.S. Pat. No. 4,292,272 and GB 2,087,074A, or a combination thereof.

The spreading action controller is incorporated in the porous spreading layer. The spreading action controller controls the spreading of an aqueous liquid sample in the spreading layer so as not to spread too broadly, and is selected from hydrophilic polymers or nonionic surfactants.

The hydrophilic polymers are polyvinyl pyrrolidone, polyvinyl alcohol, polyacrylamide, polyacrylic acid, hydrophilic cellulose derivatives, and the like. The hydrophilic cellulose derivatives are cellulose ethers in which a part of or whole hydroxyl groups of cellulose are converted to ethers by introducing lower alkyl groups having a carbon number of 1 to 3 or hydroxyl group-substituted lower alkyl groups having a carbon number of 1 to 4. Examples of such a cellulose ether are water-soluble, and include methyl cellulose, ethyl cellulose, hydroxyethyl cellulose, hydroxypropyl methyl cellulose and hydroxybutyl methylcellulose. Preferable hydrophilic polymers are polyvinyl pyrrolidone, polyvinyl alcohol and water-soluble cellulose ethers. Two or more hydrophilic polymers may be combined in use. The content of the hydrophilic polymer in the porous spreading layer is about 0.5 to about 15 g/m$^2$, preferably about 0.7 to about 10 g/m$^2$.

The nonionic surfactants are polyhydric alcohol ester ethylene oxide adducts (condensate), polyethylene glycol monoesters, polyethylene glycol diesters, higher alcohol ethylene oxide adducts (condensate), alkylphenol ethylene oxide adducts (condensate) higher fatty acid alkanol amides and the like. Examples of the nonionic surfactant are:

POE (20) sorbitan monooleate
POE (10) sorbitan monooleate
POE (4) sorbitan tristearate
POE (4) trioleate
POE (30) stearate
POE (40) stearate
POE (100) stearate
PEG (400) monostearate
PEG (400) monolaurate
PEG (1000) dilaurate
PEG (1540) distearate
Lauryl alcohol EO 6 moles condensate
Lauryl alcohol EO 10 moles condensate
Lauryl alcohol EO 30 moles condensate
Oleyl alcohol EO 20 moles condensate
Cetyl alcohol EO 20 moles condensate
POE (10) octylphenyl ether
POE (15) octylphenyl ether
POE (30) octylphenyl ether
POE (12) nonylphenyl ether
POE (20) nonylphenyl ether
Triethanolamine oleate As used herein POE=polyethylene oxide, PEG=polyethylene glycol, EO=ethylene oxide. The number in parentheses represents the condensation number of ethylene oxide units.

Two or more nonionic surfactants may be combined in use. When a nonionic surfactant is combined with a hydrophilic polymer, HLB value of the nonionic surfactant is preferably more than 10. The content of nonionic surfactant in the porous spreading layer is about 0.1 to about 3 $g/m_2$, preferably about 0.2 to 2 $g/m^2$.

In the cases of analytical elements for analysis of calcium, an acid for decomposing the calcium compounds in a sample is preferably dissolved in an organic solvent which does not dissolve the indicator selected from those previously mentioned. The calcium compounds include protein-bound, such as, albumin-bound calcium compounds and acid-bound calcium compounds, such as calcium phosphate. Heretofore, the error caused by calcium phosphate has not been recognized as a problem. The present inventors have found that the analytical value of calcium concentration becomes lower with increasing phosphate concentration. In the case of the analytical element of the invention, the exact analytical value can be obtained, though phosphate concentration is relatively high.

In order to decompose protein-bound calcium, the pH is preferably lower than 4, while, in order to decompose calcium phosphate, the pH is preferably at about 1 to 2. Since a pH buffer is not incorporated in the porous spreading layer, the pH of this layer can be adjusted to such a low range by adding a small amount of an acid. The acid may be incorporated into the porous spreading layer in the form of a suspension. Examples of the acid are fatty acids, such as, monocarboxylic acids, including acetic acid and dicarboxylic acids, including malonic acid, glutaric acid, adipic acid and pimelic acid, halogensubstituted fatty acids, such as, monochloroacetic acid and trichloroacetic acid, aromatic carboxylic acids, such as, phthalic acid, aliphatic hydroxycarboxylic acids, such as, lactic acid, malic acid and citric acid, aromatic hydroxycarboxylic acids, such as, salicylic acid and sulfonic acids, such as, sulfosalicylic acid and 1,5-naphthalenedisulfonic acid. Two or more acids may be combined, if necessary. In the spreading layer of the analytical element for analysis of calcium, a quaternary amine polymer or the like may be incorporated, and inorganic phosphorus, such as, phosphate ions released by the acid treatment are trapped by this polymer.

In such an analytical element, the bound state calcium, such as, protein-bound calcium and calcium phosphate compounds are decomposed by action of the acid incorporated in the spreading layer to generate calcium ion. While the calcium in an ion state passes through the spreading layer as it is. The acid accompanied with calcium ion is neutralized with the pH buffer incorporated in the reagent layer or other layers, and adjusted around the optimum pH of color reaction. Then, total calcium ion reacts with the indicator to produce a detectable optical change and the object calcium content can be determined by detecting this optical change. Other layers may be incorporated in the analytical element.

For example, a water-absorption layer may be provided between the support and the reagent layer. The water-absorption layer is mainly composed of a hydrophilic polymer which absorbs water to swell, and it absorbs the water of an aqueous liquid sample which reaches the surface of this layer. In the case of a whole blood sample, it accelerates the permeation of the blood plasma component into the reagent layer. The hydrophilic polymer is selected from those mentioned previously. In general, gelatin, a gelatin derivative, polyacrylamide and polyvinyl alcohol are preferable, gelatin being the most preferred. The dry thickness of the water-absorption layer is about 3 $\mu$m to about 100 $\mu$m, preferably about 5 $\mu$m to about 30 $\mu$m. The coating weight of the water-absorption layer itself is about 3 $g/m^2$ to about 100 $g/m^2$, preferably about 5 $g/m^2$ to about 30 $g/m^2$. A pH buffer selected from those described previously or a base polymer may be incorporated in the water-absorption layer. A nonionic surfactant and a known mordant or polymer mordant may also be incorporated.

A hydrophilic nonporous intermediate layer may be provided between the porous spreading layer and the reagent layer. This layer inhibits permeation of proteins, such as, albumin and globulin, and it is composed of a hydrophilic polymer as mentioned previously or crosslinked thereof. Preferable hydrophilic polymers are gelatin, gelatin derivatives, polyacrylamide and polyvinyl alcohol, and gelatin, particularly deionized gelatin is the most preferable. Examples of crosslinking agents are vinylsulfonyl crosslinking agents, such as, 1,2-bis(vinylsulfonylacetamide)ethane and bis(vinylsulfonylmethyl) ether and aldehydes for gelatin, and aldehydes and two glycidyl groups containing epoxy compounds for methallyl alcohol copolymer.

The dry thickness of the intermediate layer is about 3 $\mu$m to about 20 $\mu$m, preferably about 5 $\mu$m to 15 $\mu$m. In this layer, a pH buffer mentioned previously or a known base polymer and a nonionic surfactant may be added. Light-reflecting particles, such as, titanium dioxide particles or barium sulfate particles may be suspended, and it also functions as a light-reflecting layer. The light-reflecting layer may be provided separately. The dry thickness of the light-reflecting layer is about 5 $\mu$m to about 50 $\mu$m, preferably about 7 $\mu$m to about 30 $\mu$m. The coating weight of the light-reflecting layer itself is about 5 $g/m^2$ to about 50 $g/m^2$, preferably about 7 $g/m^2$ to about 30 $g/m^2$.

An adhesive layer may be provided in order to fortify the adhesive force to the spreading layer. This layer is composed of the hydrophilic polymer mentioned previously, such as gelatin, and its dry thickness is about 0.5 $\mu$m to about 5 $\mu$m.

The method of the invention is characterized by incorporating the spreading action controller or the acid mentioned previously using an organic solvent which does not dissolve the water-soluble indicator incorporated in the reagent layer. Such a solvent is usually a polar solvent having a boiling point of lower than 100° C., and includes aliphatic alcohols, such as, methanol, ethanol, propanol, butanol and isopropanol, dialkylketones, such as, acetone and methyl ethyl ketone, dialkyl ethers, such as, diethyl ether, aliphatic cyclic ethers, such as, tetrahydrofuran and dioxane. Some nonpolar solvents, such as, acetonitrile, benzene and hexane are also included. Among these, aliphatic alcohols are preferable, and low toxic alcohols, such as, ethanol, propanol, butanol and isopropanol are particularly preferable in view of working circumstances. For example, when o-Cresolphthalein is employed as the indicator for analysis of calcium, the above alcohols are suitable. This compound itself is slightly soluble in water but readily soluble in alcohols. However, near its optimum pH (pH 10.5), its is readily soluble in water but insoluble in alcohols.

The concentration of the spreading action controller is preferably high, such as, about 0.2% to about 10%, particularly, about 0.3% to about 7%. A small amount of water may be added to the spreading action controller solution so as to prevent migration of the water-soluble indicator to the spreading layer. The spreading action controller solution may be applied or sprayed uniformly on the spreading layer. When both a hydrophilic polymer and a nonionic surfactant are incorporated, a mixed solution of the two may be used. They may also be incorporated separately. In the case of the acid, a suspension of the acid may be used instead of its solution.

The application or spraying is preferably carried out after the spreading layer is incorporated into the analytical element. When the spreading layer is a membrane filter (blushed polymer layer), knitted fabric or woven fabric, the solution or suspension may be added to the spreading layer prior to its lamination. However, in this case, it is difficult to adjust the content of the spreading action controller or the acid to a prescribed value.

After the application or spraying, the analytical element is dried under reduced pressure, by air-drying or the like.

Other processes for preparing the analytical element of the invention may be used.

The integral multilayer analytical element of the invention is preferably cut into square or circular pieces having a side or diameter of about 15 mm to about 30 mm, and put in a slide frame disclosed in U.S. Pat No. 4,169,751, Japanese Patent No. 57-63452, U.S. Pat No. 4,387,990 and Japanese Utility Model Kokai No. 58-32350, PCT application No. WO 83/00391, etc. for use.

The measurement is carried out, for example, according to the manner disclosed in the specifications of the abovementioned patents. About 5 $\mu$l to about 30 $\mu$l preferably about 8 $\mu$l to about 15 $\mu$l of an aqueous sample is spotted on the spreading layer, and incubated at a definite temperature in the range of about 20° C. to about 45° C. for 1 to 10 minutes. Thereafter, a detectable change, such as, the color change or coloring in the multilayer analytical element is measured from the side of the support through reflection photometry, and the subject component in the sample is determined by the principle of colorimetry. When this measurement is carried out by using the chemical-analytical apparatus disclosed in U.S. Pat. Nos. 4,488,810 and 4,424,191, highly accurate results can easily be obtained by a simple operation.

In the method of the present invention, the migration of the water-soluble indicator in the reagent layer at the time of incorporating the spreading action controller or the acid into the spreading layer is inhibited by using a particular organic solvent. Migrations of the indicator and colored material to the spreading layer are also lowered by the spreading action controller, and, as a result, the analytical accuracy of the analytical element is improved. In the case of the analytical element for analysis of calcium, permeation of the acid into other layers than the spreading layer is inhibited, and permeation of a pH buffer into other layer(s) into the spreading layer is also inhibited by using a particular organic solvent. As a result, effective decomposition of calcium compounds in a sample and effective coloration can be achieved.

EXAMPLES

EXAMPLE 1

The support employed was a colorless transparent polyethylene terephthalate (PET) film having a thickness of 180 $\mu$m. The following layers were successively coated and dried to form a laminate.

| Water-absorption layer: | |
|---|---|
| Deionized gelatin | 4.8 g/m$^2$ |
| nonylphenoxypolyethoxyethanol (containing 10 hydroxyethylene units on average) | 0.11 g/m$^2$ |
| 1,2-bis(vinylsulfonylacetamide)ethane | 0.5 g/m$^2$ |
| The aqueous solution was adjusted to pH 6.5 by using NaOH. | |
| Reagent layer: | |
| Deionized gelatin | 23.9 g/m$^2$ |
| polyoxyethylene nonyl phenyl ether (containing 10 hydroxyethylene units on average) | 0.41 g/m$^2$ |
| CAPS | 3.81 g/m$^2$ |
| o-Cresolphthalein Complexone | 0.15 g/m$^2$ |
| 8-hydroxyquinolin-5-sulfonic acid | 0.54 g/m$^2$ |
| The aqueous solution was adjusted to pH 10.6 by using NaOH. | |
| Adhesive layer: | |
| Deionized gelatin | 1.46 g/m$^2$ |
| Polyoxyethylene nonyl phenyl ether (containing 10 hydroxyethylene units on average) | 0.10 g/m$^2$ |
| titanium dioxide particles | 0.85 g/m$^2$ |

The adhesive layer was uniformly dampened with water, and a PET tricot fabric cloth knitted from 100S PET spun yarn having a mean thickness of 250 $\mu$m was pressed to laminate thereon as the spreading layer. Subsequently, the following polymer ethanol solution was applied on the spreading layer and dried to obtain the integral multilayer analytical element for analysis of calcium.

| Polymer ethanol solution: | |
|---|---|
| Polyvinyl pyrrolidone (mean molecular weight 360,000) | 1.01 g/m$^2$ |
| polyoxyethylene nonyl phenyl ether (containing 40 hydroxyethylene units on average) dissolved in ethanol. | 2.11 g/m$^2$ |

COMPARATIVE EXAMPLE 1

An integral multilayer analytical element for analysis of calcium was prepared in the same manner as Example 1, except for the following: The content of o-Cresolphthalein Complexone in the reagent layer was increased from 0.15 g/m$^2$ to 0.46 g/m$^2$, and the content of 8-hydroxyquinoline-5-sulfonic acid in the reagent layer was increased from 0.54 g/m$^2$ to 1.65 g/m$^2$. Instead of the polymer ethanol solution, the following aqueous polymer solution was employed.

| Aqueous polymer solution: | |
|---|---|
| Methyl cellulose (viscosity of 2% aqueous solution at 20° C.; 100 cps) | 5.75 g/m$^2$ |
| nonylphenoxypolyethoxyethanol (containing 40 hydroxyethylene units on average) | 7.44 g/m$^2$ |
| titanium dioxide particles | 15.5 g/m$^2$ |
| dissolved and suspended in water, and applied. | |

EXAMPLE 2

The integral multilayer analytical elements prepared in Example 1 and Comparative Example 1 were evaluated by using a commercial control serum "Monitrol IX" (DADE, U.S.A.), and the results are shown in Table 1. As shown in the Table, in the case of the analytical element of Example 1, dispersion of the measured values are remarkably small.

TABLE 1

| | Example 1 | | Comparative 1 |
|---|---|---|---|
| Run No. | Measured Value mg/dl | Run No. | Measured Value mg/dl |
| 1 | 7.7 | 1 | 7.9 |
| 2 | 7.7 | 2 | 7.6 |
| 3 | 7.7 | 3 | 7.9 |
| 4 | 7.8 | 4 | 7.7 |
| 5 | 7.9 | 5 | 7.7 |
| 7 | 7.7 | 7 | 7.6 |
| 8 | 7.8 | 8 | 7.6 |
| 9 | 7.8 | 9 | 7.4 |
| 10 | 7.6 | 10 | 7.6 |
| 11 | 7.8 | 11 | 7.6 |
| 12 | 7.7 | 12 | 7.9 |
| 13 | 7.7 | 13 | 7.6 |
| 14 | 7.7 | 14 | 7.7 |
| 15 | 7.8 | 15 | 7.7 |
| 16 | 7.8 | 16 | 7.7 |
| 17 | 7.8 | 17 | 7.4 |
| 18 | 7.7 | 18 | 7.6 |
| 19 | 7.7 | 19 | 7.4 |
| 20 | 7.6 | 20 | 7.5 |
| 21 | 7.6 | 21 | 7.5 |
| 22 | 7.7 | 22 | 7.7 |
| 23 | 7.8 | 23 | 7.6 |
| 24 | 7.8 | 24 | 7.5 |
| 25 | 7.7 | 25 | 7.7 |
| Average | 7.74 | Average | 7.63 |
| SD | 0.0757 | SD | 0.1406 |
| CV | 0.98% | CV | 1.8% |

EXAMPLE 3

The following layers were successively applied on a colorless transparent PET film having a thickness of 180 μm, and dried to form a laminate.

| Reagent layer: | |
|---|---|
| Deionized gelatin | 16.8 g/m$^2$ |
| nonylphenoxypolyethoxyethanol (containing 10 hydroxyethylene units on average) | 1.1 g/m$^2$ |
| CAPS | 2.8 g/m$^2$ |
| o-Cresolphthalein Complexone | 0.15 g/m$^2$ |
| 8-hydroxyquinoline-5-sulfonic acid | 0.56 g/m$^2$ |
| The aqueous solution was adjusted to pH 10.6 by using NaOH. | |
| Adhesive layer: | |
| Deionized gelatin | 1.46 g/m$^2$ |
| nonylphenoxypolyethoxyethanol (containing 10 hydroxyethylene units on average) | 0.10 g/m$^2$ |
| titanium dioxide | 0.85 g/m$^2$ |
| The aqueous solution was adjusted to pH 10.6 by using NaOH. | |

The adhesive layer was uniformly dampened with water, and a tricot knitted fabric cloth was pressed to laminate thereon as the spreading layer. Subsequentially, the following polymer ethanol solution was applied on the spreading layer, and dried to obtain the integral multilayer analytical element for analysis of calcium.

| Polymer ethanol solution: | |
|---|---|
| Polyvinyl pyrrolidone (mean molecular weight 360,000) | 4.1 g/m$^2$ |
| nonylphenoxypolyethoxyethanol (containing 10 hydroxyethylene units on average) | 8.6 g/m$^2$ |
| trichloroacetic acid dissolved in ethanol. | 0.9 g/m$^2$ |

COMPARATIVE EXAMPLE 2

An integral multilayer analytical element was prepared in the same manner as Example 3 except trichloroacetic acid was not added to the polymer ethanol solution.

EXAMPLE 4

Calcium concentrations of the following Solution 1 and Solution 2 were measured by using the analytical elements prepared in Example 3 and Comparative Example 2.

Solution 1: Aqueous solution containing 10 mg/ml of calcium (CaCl$_2$ was used).

Solution 2: Aqueous solution containing 10 mg/ml of calcium (CaCl$_2$ was used) and 10 mg/l of phosphorus (Na$_2$HPO$_4$ was used). Since the solution became turbid, it was stirred vigorously before each sampling.

The results are shown in Table 2.

TABLE 2

| | Example 3 | Comparative 2 |
|---|---|---|
| Solution 1 | 10.0 mg/dl | 10.0 mg/dl |
| Solution 2 | 9.4 mg/dl | 6.2 mg/dl |

As shown in the table, the negative error in the case of using Example 3 in the presence of phosphorus is less than one sixth of that of Comparative product 2.

EXAMPLE 5

An integral multilayer analytical element was prepared in the same manner as Example 3, except 0.9 g/m$^2$ of trichloroacetic acid in the polymer ethanol solution was replaced by 0.6 g/m$^2$ of citric acid. The calcium concentrations of Solution 1 and Solution 2 were measured by using this analytical element, and similar results to Example 4 were obtained.

What is claimed is:

1. An integral multilayer analytical element for analysis of calcium compounds comprising, in this order, a water-impermeable light-transmissive support, a reagent layer containing a water-soluble indicator capable of reacting with an analyte containing calcium to produce an optically detectable change, and a porous spreading layer containing an acid capable of decomposing the calcium compound in a sample, and a pH buffer capable of maintaining the reaction with said indicator at its optimum pH incorporated in said reagent layer or an intermediate layer between said reagent layer and said porous spreading layer.

2. The integral multilayer analytical element of claim 1 wherein said porous spreading layer contains a spreading action controlling agent.

3. A method of analyzing calcium compounds with comprises spotting an aqueous liquid sample on a spreading layer of an integral multilayer analytical element for analysis of calcium comprising, in this order, a water-impermeable light-transmissive support, a reagent layer containing a water-soluble indicator capable of reacting with an analyte containing calcium to produce an optically detectable change, and a porous spreading layer containing an acid capable of decomposing the calcium compound in a sample, and a pH buffer capable of maintaining the reaction with said indicator at its optimum pH incorporated in said reagent layer or an intermediate layer between said reagent layer and said porous spreading layer, releasing calcium ion from said calcium compound in the presence of said acid contained in said spreading layer, producing said optically detectable change by supplying said acid treated sample to said reagent layer to interact with said indicator, and detecting said change optically.

* * * * *